US00PP33178P2

(12) United States Plant Patent
Hochberg

(10) Patent No.: US PP33,178 P2
(45) Date of Patent: Jun. 22, 2021

(54) ***LAGERSTROEMIA* PLANT NAMED 'HOCH1065'**

(50) Latin Name: *Lagerstroemia indica*
Varietal Denomination: HOCH1065

(71) Applicant: Hochberg Ornamental Export Plants Ltd, Moshav Bitzaron (IL)

(72) Inventor: Omer Hochberg, Moshav Bitzaron (IL)

(73) Assignee: Hochberg Ornamental Export Plants Ltd

( * ) Notice: Subject to any disclaimer, the term of this patent is extended or adjusted under 35 U.S.C. 154(b) by 0 days.

(21) Appl. No.: 17/094,151

(22) Filed: Nov. 10, 2020

(51) Int. Cl.
*A01H 5/02* (2018.01)
*A01H 6/00* (2018.01)

(52) U.S. Cl.
USPC ..... Plt./252
CPC ..... *A01H 6/00* (2018.05)

(58) Field of Classification Search
USPC ..... Plt./252
CPC ..... A01H 6/00
See application file for complete search history.

*Primary Examiner* — Anne Marie Grunberg
(74) *Attorney, Agent, or Firm* — Cassandra Bright

(57) ABSTRACT

A new and distinct cultivar of *Lagerstroemia* plant named 'HOCH1065' is disclosed, characterized by purple flowers and dark green foliage. Plants are free branching and bushy. The new variety is a *Lagerstroemia*, normally used for outdoor ornamental purposes.

1 Drawing Sheet

Latin name of the genus and species: *Lagerstroemia indica.*

Variety denomination: 'HOCH1065'

BACKGROUND OF THE INVENTION

The new *Lagerstroemia* cultivar is a product of a planned breeding program conducted by the inventor, in Moshav Bitzaron, Israel. The objective of the breeding program was to develop new Crepe Myrtle plants for ornamental purposes. The cross resulting in this new variety was made during July of 2015.

The seed parent is the unpatented proprietary variety referred to as *Lagerstroemia* 'L101'. The pollen parent is the unpatented proprietary variety referred to as *Lagerstroemia* 'L88'.The new variety was selected in August of 2016 by the inventor in a group of seedlings resulting from the 2015 crossing, in a nursery in Moshav Bitzaron, Israel. Date of first sale was Jan. 1, 2020, occurring in Europe. This sale was made directly by the inventor or one who obtained the claimed invention directly or indirectly from the inventor. This sale and all public disclosures made between Jan. 1, 2020 and the filing of this application fall within the exception allowed under 102(b)(1).

Asexual reproduction of the new cultivar was performed by softwood cuttings. This was first performed at the same nursery in Moshav Bitzaron, Israel during June of 2017, and has shown that the unique features of this cultivar are stable and reproduced true to type in multiple successive generations.

SUMMARY OF THE INVENTION

The cultivar 'HOCH1065' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'HOCH1065' These characteristics in combination distinguish 'HOCH1065' as a new and distinct *Lagerstroemia* cultivar:

1. Purple blooms.
2. Deep green foliage.
3. Good branching.
4. Bushy plant habit, reaching 80 to 100 cm in the second year.

PARENT COMPARISON

Plants of the new cultivar 'HOCH1065' are similar to plants of the seed parent in most horticultural characteristics; however, plants of the new cultivar 'HOCH1065' differ in the following;

1. The new variety has purple flowers, while the seed parent has white flowers.

Plants of the new cultivar 'HOCH1065' are similar to plants of the pollen parent in most horticultural characteristics; however, plants of the new cultivar 'HOCH1065' differ in the following;

1. The new variety has purple flowers, while the pollen parent has white flowers.
2. The new variety has an upright and outward shrubby plant form; the pollen parent is mounding.

COMMERCIAL COMPARISON

Plants of the new cultivar 'HOCH1065' are comparable to the commercial variety *Lagerstroemia* 'Purple Velvet', unpatented. The two *Lagerstroemia* varieties are similar in most horticultural characteristics; however, the new variety 'HOCH1065' differs in the following;

1. The new variety has lighter purple blooms than this comparator.

2. The new variety has darker foliage than this comparator.

Plants of the new cultivar 'HOCH1065' are comparable to the commercial variety *Lagerstroemia* 'Rhapsody in Pink', U.S. Plant Pat. No. 16,616. The two *Lagerstroemia* varieties are similar in most horticultural characteristics; however, the new variety 'HOCH1065' differs in the following;

1. The new variety has purple blooms, while this comparator pink blooms.
2. The new variety has lighter colored foliage than this comparator.

BRIEF DESCRIPTION OF THE PHOTOGRAPH

The accompanying photograph illustrates a typical flowering plant of 'HOCH1065' grown outdoors in Moshav Bitzaron, Israel. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015 except where general terms of ordinary dictionary significance are used. The following observations and measurements describe 'HOCH1065' plants grown outdoors in Visalia, Calif. The growing temperature ranged from approximately 18° C. to 38° C. during the day and from approximately 5° C. to 10° C. during the night. General light conditions are normal sunlight and numerical values represent averages of typical plant types.

Botanical classification: *Lagerstroemia indica* 'HOCH1065'.

PROPAGATION

Type of propagation typically used: Softwood cuttings.
Time to initiate roots: 21 days at 18-27° C.
Time to produce a rooted cutting: 1-2 months at 18-27° C.
Root description: Thin fibrous, dense, moderate branching. White in color, not accurately measured with R.H.S. Chart.

PLANT

Age of plant described: About 1.5 years old from a rooted cutting.
Container size: 3 gallon container.
Growth habit: Upright and outward. Free branching.
Plant spread: 50 cm.
Plant height: 60 cm.
Plant vigor: Very good.
Length of primary lateral branches: Varies as the plant is often pruned. 10 to 25 cm on average.
Diameter of lateral branches: 4 to 6 mm.
Quantity of lateral branches: About 12 to 18.
Stem:
- *Color*.—New growth: Near RHS Greyed-Purple 185A lightly streaked Greyed-green 197D. Old growth: Near RHS Grey-Brown N199B, flushed 187B.
- *Shape*.—Round.
- *Strength*.—Flexible and very strong.
- *Aspect angle*.—Upright with slight outward arch.
- *Texture*.—Very slightly pubescent, then slightly scaly with age.

Internode length.—Average range 1.1 to 3.0 cm.
Bark peel: Base of the oldest wood develops a slightly scaly, non-peeling bark colored near Grey-Green 197A striated Grey-Brown 199B.

FOLIAGE

Leaf:
- *Average length*.—5.2 cm.
- *Average width*.—2.7 cm.
- *Shape of blade*.—Ovate.
- *Apex*.—Acute.
- *Base*.—Obtuse.
- *Margin*.—Entire.
- *Aspect*.—Slightly to moderately undulate.
- *Texture of top surface*.—Smooth.
- *Texture of bottom surface*.—Smooth.
- *Color*.—Young foliage upper side: Near RHS Green 139A margin Red-Purple 59A. Young foliage under side: Near RHS Yellow-Green 146A margin Red-Purple 59A. Mature foliage upper side: Near RHS Green 136B, margin Greyed-Purple 187A. Mature foliage under side: Near RHS Yellow-Green 147B margin Greyed-Purple 187B. Fine stippling throughout blade near 187B. Venation: Type: Pinnate. Venation color upper side: Near RHS Yellow-Green N144A, heavily flushed 187D. Venation color under side: Near RHS Yellow-Green N144A, heavily flushed 187D.
- *Petiole*.—Length: 1-2 mm. Diameter: 1-2 mm. Texture, upper side: Smooth. Texture, under side: Smooth. Color, upper side: Near RHS Green 136A. Color, under side: Near RHS Green 136A.

FLOWER

Natural flowering season: Summer through Fall. Begins flowering mid-June in California.
Inflorescence form: Panicles.
Flowers per inflorescence: About 40 to 80 flowers and buds.
Inflorescence size:
- *Width*.—11 cm.
- *Length*.—Average 16 cm.

Individual flowers:
- *Type*.—Rotate.
- *Shape*.—Obovate.
- *Habit*.—Whorled outward.
- *Diameter*.—3.0 cm.
- *Depth*.—2.8 cm.
- *Persistence*.—Self-cleaning.
- *Fragrance*.—Faint musty scent.

Petals:
- *Arrangement*.—Whorled.
- *Number*.—6.
- *Shape*.—Overall irregular orbicular.
- *Aspect*.—Deeply undulate.
- *Margin*.—Deeply ruffled, crenate.
- *Tip shape*.—Rounded.
- *Base shape*.—Rounded.
- *Length*.—1.4 cm, undulated, cannot unfold.
- *Width*.—1.3 cm, undulated, cannot unfold.
- *Texture*.—Upper: Glabrous. Lower: Glabrous.
- *Color*.—When opening: Upper surface: Near RHS Purple N78A. Under surface: Near RHS Purple N78A. Fully opened: Upper surface: Near RHS Violet-Purple N81A with interior overlay-flushed Purple N78A. Under surface: Near RHS Violet-Purple N81A with interior overlay-flushed Purple N78A.

Bud:

*Shape*.—Sphere.
*Length*.—9 mm.
*Diameter*.—7 mm.
*Color*.—Near RHS Greyed-Purple 187C, base Yellow-Green 145A.

Calyx:

*Shape*.—Fused into a conical shape.
*Length*.—7 mm.
*Diameter*.—7 mm.

Sepals:

*Appearance*.—Matte.
*Arrangement*.—Rotate, fused.
*Shape*.—Narrowly triangular.
*Tip shape*.—Acute.
*Base shape*.—Obtuse.
*Margin*.—Entire.
*Quantity per flower*.—6.
*Length*.—7 mm.
*Width*.—3-4 mm.
*Margin*.—Entire.
*Texture*.—Inner: Smooth. Outer: Smooth, coriaceous.
*Color*.—Inner: Near RHS Yellow-Green 144D. Base near Greyed-Purple 183C. Lower: Near RHS Greyed-Purple 184A.

Peduncle:

*Length*.—Average range 2.0 to 3.0 cm.
*Diameter*.—3-4 mm.
*Texture*.—Slightly pubescent.
*Color*.—Near Greyed-Purple 187B.
*Orientation*.—Upright.
*Strength*.—Strong and flexible.

Pedicel:

*Length*.—3 to 7 mm.
*Diameter*.—1-2 mm.
*Angle*.—About 45 degrees from attachment.
*Strength*.—Moderate.
*Texture*.—Slightly pubescent.
*Color*.—Near Green 138B flushed Greyed-Purple 187B.

REPRODUCTIVE ORGANS

Stamens:

*Number*.—About 20-30, curled and congested.
*Filament length*.—About 7 mm, when pulled straight.
*Filament color*.—Near Yellow 2D.

Anthers:

*Shape*.—Curled.
*Length*.—1 mm.
*Color*.—Yellow 13A.
*Pollen*.—Scant to none observed. Colored near Yellow 13A.

Pistil:

*Number*.—1.
*Length*.—1.8 cm.

Stigma:

*Shape*.—Globular.
*Color*.—Near RHS Greyed-Purple 185B.
*Ovary color*.—Near RHS Yellow 2D.

OTHER CHARACTERISTICS

Fruits and seeds: Not observed to date.

Disease/pest resistance: Neither resistance nor susceptibility to normal diseases and pests of *Lagerstroemia* observed.

Temperature range: Observed to tolerate a temperature range from −28° C. to 35° C. Root hardy to −28 C, top of the plant does die back to the ground.

What is claimed is:

1. A new and distinct cultivar of *Lagerstroemia* plant named 'HOCH1065' as herein illustrated and described.

* * * * *

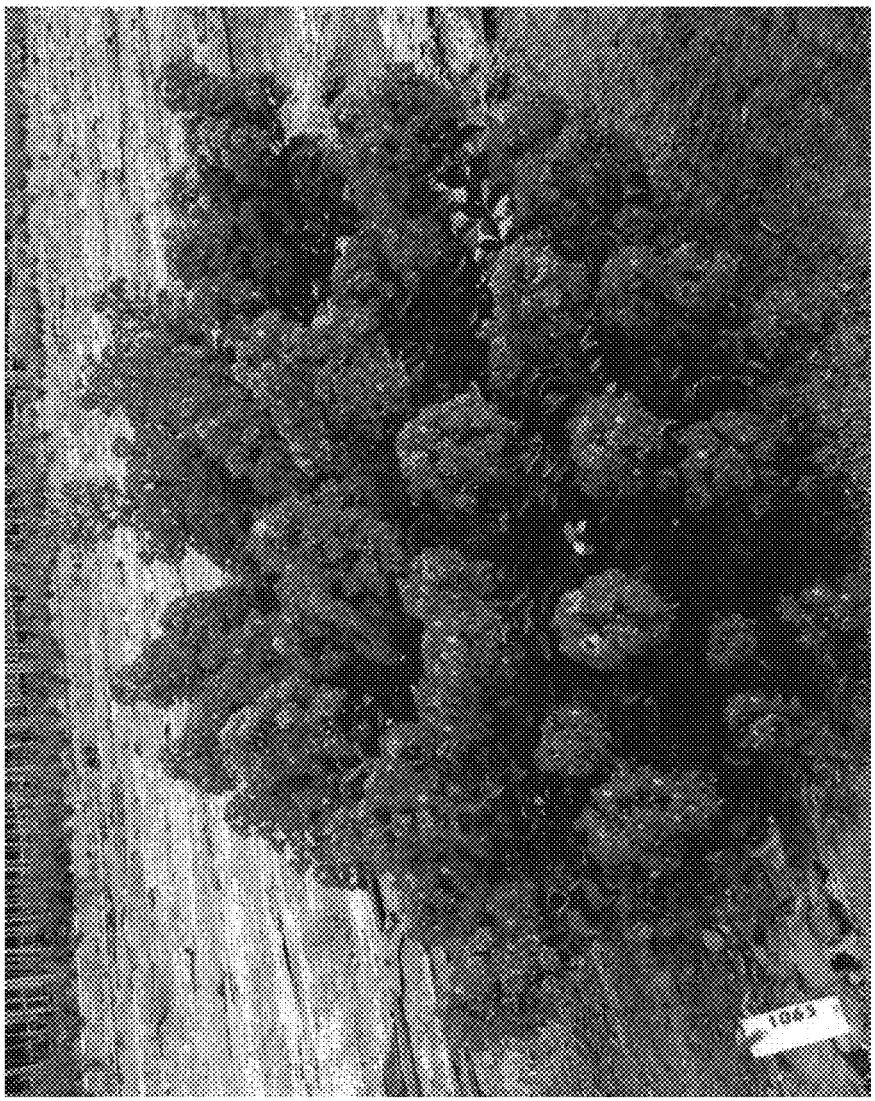
1063